United States Patent
Hsu et al.

(10) Patent No.: US 10,490,052 B2
(45) Date of Patent: Nov. 26, 2019

(54) MOTION-SENSING FLOOR MAT, MOTION-SENSING FLOOR MAT ASSEMBLY, AND MONITORING SYSTEM WITH THE SAME FLOOR MATS

(71) Applicants: SEDA CHEMICAL PRODUCTS CO., LTD., New Taipei (TW); SEDA G-Tech CO., LTD., New Taipei (TW)

(72) Inventors: Yeh-Liang Hsu, Taoyuan (TW); Wei-Kuan Wang, New Taipei (TW); Kai-Wei Chang, Miaoli County (TW); Yu-Wei Liu, New Taipei (TW); Wei-Yi Chang, Taipei (TW)

(73) Assignees: SEDA CHEMICAL PRODUCTS CO., LTD., New Taipei (TW); SEDA G-TECH CO., LTD., New Taipei (TW)

( * ) Notice: Subject to any disclaimer, the term of this patent is extended or adjusted under 35 U.S.C. 154(b) by 155 days.

(21) Appl. No.: 15/704,147

(22) Filed: Sep. 14, 2017

(65) Prior Publication Data
US 2018/0012475 A1  Jan. 11, 2018

Related U.S. Application Data

(63) Continuation-in-part of application No. 14/681,308, filed on Apr. 8, 2015, now abandoned.

(30) Foreign Application Priority Data

Jun. 16, 2014  (TW) .............................. 103120735 A

(51) Int. Cl.
*A61B 5/11* (2006.01)
*G01L 5/22* (2006.01)
(Continued)

(52) U.S. Cl.
CPC ........ *G08B 21/0469* (2013.01); *A47L 23/266* (2013.01); *A61B 5/1112* (2013.01);
(Continued)

(58) Field of Classification Search
CPC ... A61B 5/6892; A61B 5/1117; A61B 5/1113; A61B 5/1112; A61B 5/747;
(Continued)

(56) References Cited

U.S. PATENT DOCUMENTS 7,436,325 B2 * 10/2008 Bailey ...................... B60N 3/04
                                                            341/176
8,602,949 B2 * 12/2013 Pelletter ............... A63B 69/004
                                                            434/247
(Continued)

OTHER PUBLICATIONS

Pitts, Robert, "Breadth-First Traversal of a Tree," 2000, Boston University CAS CS, <http://www.cs.bu edu/teaching/c/tree/breadth-first/>.
(Continued)

*Primary Examiner* — Jacques M Saint Surin
(74) *Attorney, Agent, or Firm* — Bacon & Thomas, PLLC

(57) ABSTRACT

A motion-sensing floor mat, an assembly of such floor mats, and a monitoring system with such floor mats are provided; wherein the floor mat can be joined with another such floor mat and electrically connected to a monitoring device to form the monitoring system; the monitoring device stores a queue list and a topology matrix and uses a topological algorithm to store the identification tag of each such floor mat detected into the queue list in order, to gradually establish the topology matrix for the floor mats detected; and to thereby obtain the relative positions of the floor mats detected. When any of the floor mats is subjected to pressure (e.g., when someone falls on the floor mat accidentally) and generates a sensing signal, the monitoring device can pin-
(Continued)

point the position of that floor mat (i.e., the location of the fall) rapidly according to the topology matrix.

28 Claims, 9 Drawing Sheets

(51) Int. Cl.
*A47L 23/26* (2006.01)
*A61B 5/00* (2006.01)
*G08B 21/04* (2006.01)
*G08B 13/10* (2006.01)

(52) U.S. Cl.
CPC .......... *A61B 5/1113* (2013.01); *A61B 5/1117* (2013.01); *A61B 5/6892* (2013.01); *G01L 5/228* (2013.01); *G08B 21/043* (2013.01); *A61B 5/747* (2013.01); *A61B 2560/0443* (2013.01); *A61B 2562/0247* (2013.01); *A61B 2562/04* (2013.01); *G08B 13/10* (2013.01)

(58) Field of Classification Search
CPC .... A61B 2560/0443; A61B 2562/0247; A61B 2562/04; G08B 21/043; G08B 21/0469; G08B 13/10; G01L 5/228; A47L 23/266
USPC .......................................................... 73/649
See application file for complete search history.

(56) References Cited

U.S. PATENT DOCUMENTS

| 9,130,870 | B1 | 9/2015 | Swierk et al. |
| 9,441,884 | B2* | 9/2016 | McCallum ................ F26B 9/02 |
| 9,615,746 | B2* | 4/2017 | Horseman ............ A61B 5/6887 |
| 2002/0068147 | A1* | 6/2002 | Blum ...................... A47L 23/22 |
| | | | 428/131 |
| 2008/0236275 | A1* | 10/2008 | Breed ..................... B60C 11/24 |
| | | | 73/290 V |
| 2012/0086659 | A1 | 4/2012 | Perlin et al. |
| 2015/0054649 | A1 | 2/2015 | Desgorces |
| 2018/0263565 | A1* | 9/2018 | Najafi ................... A61B 5/1116 |

OTHER PUBLICATIONS

"CS 3343/3341 Analysis of Algorithms Graph Search Breadth First" (CS 3343/3341 Analysis of Algorithms Graph Search Breadth First, University of Texas San Antonio CS 3343/3341, Oct. 31, 2012, <http://www.cs.utsa.edu/~wagner/CS3343/graphsearch/graphseach1.html>).
"The Breadth First Search Graph Traversal Algorithm" ("The Breadth First Search Graph Traversal Algorithm,"Emory, Mar. 19, 2014, <http://www.mathcs.emory.edu/~cheung/Courses/171/Syllabus/11-Graph/bfs.html>).
"Introduction to Graph with Breadth First Search (BFS) and Depth First Search (DFS) Traversal Implemented in JAVA,"Code Project, Jan. 1, 2013, <https://www.codeproject.com/Articles/32212/Introduction-to-Graph-with-Breadth-First-Search-BF>.

* cited by examiner

FIG. 10

MOTION-SENSING FLOOR MAT, MOTION-SENSING FLOOR MAT ASSEMBLY, AND MONITORING SYSTEM WITH THE SAME FLOOR MATS

FIELD OF THE INVENTION

The present invention relates to a motion-sensing device and more particularly to a motion-sensing floor mat for domestic use to, among other functions, locate a person in an indoor space, monitor the person's frequency of motion, and detect whether the person falls over; and to an assembly of such floor mats and a monitoring system with such floor mats.

BACKGROUND OF THE INVENTION

The population pyramid is changing worldwide as a result of declining birth rate and improvements in the medical environment. The percentage of the elderly population, in particular, has risen significantly. In 1950, a senior citizen was reared by an average of twelve people in the labor force. As the population pyramid changes, however, the ratio of the latter to the former is lowered on a yearly basis such that the burden on the labor force is increasing. In Taiwan, for example, the aforesaid ratio has dropped to 7:1 and is estimated to reach 2.7:1 in twenty years. More attention, therefore, should be paid to the physical and mental health and medical care of the elderly. In fact, how to create an environment where the aged can lead comfortable, cheerful, and carefree lives while those in the labor force are allowed to devote themselves to work without having to worry about the wellbeing of their senior family members is a subject that concerns us all.

Physiological aging takes place as we grow old. An aged person not only may respond more slowly to the outside world, but also may become less capable of performing various body movements. In many cases, physiological aging can cause inconvenience to a person's daily life, especially a sick person's. Such inconveniences may also give rise to danger and hence should be dealt with seriously. An elderly person, when not tended to, may topple over, bump into an object by accident, or even collapse to the ground due to a sudden physiological condition. To prevent the danger associated with any of the foregoing scenarios from escalating without timely help, more and more importance is attached to domestic safety, telecare, and like issues, and because of that, related applications and technologies are being developed rapidly. A notable example of products developed to cope with the aforesaid situations is motion-sensing floor mats.

Typically, a conventional motion-sensing floor mat is provided therein with a sensor module. When subjected to pressure, the sensor module sends a sensing signal to a monitoring device (e.g., a computer), in order for a caregiver (e.g., a family member who is working away from home or a professional caregiver in a nursing home) to know via the monitoring device the current motion of the elderly person being monitored and take necessary actions as soon as an abnormal condition is identified. While the conventional motion-sensing floor mats are helpful in notifying a caregiver of the occurrence of an accident, they have limitations in use. For example, when the conventional motion-sensing floor mats are placed over a small area, a caregiver detecting an emergency through the monitoring device can indeed go to the matted area at once to provide necessary assistance. If, however, the conventional motion-sensing floor mats are laid extensively in a house, or even in a large nursing home of several stories and with differently-sized partitioned areas on each floor, a caregiver spotting an abnormal condition through the monitoring device may have problem identifying the location of the abnormality immediately, let alone reaching the location at the earliest possible time to deal with the situation. The problem can be somewhat solved by dividing the large area into a plurality of smaller ones, monitoring each smaller area with a separate monitoring device, and using a host device to collect the information gathered by each monitoring device. Nevertheless, this truly feasible solution does not work well if the entire area to be monitored is not divided sufficiently, and dividing the entire area excessively will, on the other hand, incur a considerable increase in the expenses for purchasing the monitoring devices, which is by no means ideal.

In summary of the above, the conventional motion-sensing floor mats allow a caregiver to know the occurrence of an accident rapidly, but if such floor mats are applied to an extensive area, a caregiver will find it difficult to locate the accident immediately and hence cannot get to the site of the accident right away. It is therefore important for those in the related industry to design a monitoring system that not only incorporates motion-sensing floor mats, but also can establish a topology matrix for the motion-sensing floor mats in use so that, in addition to being alerted to the occurrence of an accident instantly, a caregiver can locate the accident without delay.

BRIEF SUMMARY OF THE INVENTION

In view of the deficiencies of the existing human body motion sensing devices in monitoring an elderly person's movement and identifying their motion, the inventor of the present invention put years of practical experience in research and development into an extensive study with numerous tests and improvements and finally succeeded in designing a motion-sensing floor mat, a motion-sensing floor mat assembly, and a monitoring system with such floor mats. The invention is intended to provide the general public with easy-to-implement, easy-to-assemble, and much safer motion-sensing floor mats and a monitored environment made possible by such floor mats.

One objective of the present invention is to provide a motion-sensing floor mat that can be joined with at least another such motion-sensing floor mat and includes a standardized base, a pressure-sensing layer, an insulating and isolating layer, and an elastic conductive layer. The standardized base has a first assembly side and a second assembly side corresponding to the first assembly side. The first assembly side is provided with a plurality of first engaging portions, and one of the first engaging portions is provided with a first information transmission module. The second assembly side is provided with a plurality of second engaging portions, and one of the second engaging portions is provided with a second information transmission module. The pressure-sensing layer is provided on the standardized base and has a plurality of sensing electrode assemblies. The sensing electrode assemblies are electrically connected to the first information transmission module and the second information transmission module and are each provided with a successively bent gap. The insulating and isolating layer covers the pressure-sensing layer and has a plurality of through holes, wherein some of the through holes are sequentially arranged along the gaps of the sensing electrode assemblies. The elastic conductive layer covers the insulating and isolating layer such that, when a portion of the elastic conductive layer is compressed by an external force, the compressed portion of the elastic conductive layer is brought into contact with the pressure-sensing layer through the corresponding through holes. Thus, using a non-conscious sensing method, the motion-sensing floor mat can monitor the interaction between an elderly person and an indoor environment continuously.

Another objective of the present invention is to provide a motion-sensing floor mat assembly that includes a plurality of the foregoing motion-sensing floor mats, wherein the floor mats can be joined arbitrarily to adapt to the size of a user's domestic space, thereby enabling long-term, continuous monitoring of the space.

Still another objective of the present invention is to provide a monitoring system that includes a plurality of the foregoing motion-sensing floor mats and a monitoring device. The motion-sensing floor mats can be joined arbitrarily into various configurations, and the monitoring device can obtain the relative positions of the motion-sensing floor mats rapidly by means of a topological algorithm so that, when someone falls down on the floor mats, a caregiver can know the location of the fall rapidly via the monitoring device and provide necessary medical care as soon as possible.

BRIEF DESCRIPTION OF THE SEVERAL VIEWS OF THE DRAWINGS

The objectives, technical features, and effects of the present invention can be better understood by referring to the following detailed description of some illustrative embodiments in conjunction with the accompanying drawings, in which:

FIG. 10 schematically shows how a queue list and a topology matrix are established through a topological algorithm of the present invention.

DETAILED DESCRIPTION OF THE INVENTION

The present invention mainly provides a motion-sensing floor mat for use in a domestic environment. The motion-sensing floor mat is characterized in that it incorporates a motion-sensing technique into a floor mat structure, that a plurality of such floor mats can be freely joined together to meet the actual requirements of an indoor space, and that after assembly of a plurality of such floor mats, the location of each floor mat can be rapidly identified. The invention uses a non-conscious sensing method to not only determine the indoor location of an elderly person, child, or person with mobility impairment, but also monitor the person's movement.

More specifically, the motion-sensing floor mat of the present invention has a main sensing unit covered with a soft and resilient conductive surface layer. This conductive surface layer and the underlying pressure-sensing layer jointly form a piezoresistive sensor. During a long-term, continuous monitoring operation, therefore, the motion (e.g., walking, standing still, being seated, or toppling over) of an elderly person, child, or person with mobility impairment can be determined based on the relationship between the pressure applied to a single motion-sensing floor mat or multiple such floor mats and the resistance value(s) output therefrom. Moreover, the monitoring operation does not interfere with the daily life of the person being monitored at all.

The structural features and method of use of the present invention are described below with reference to specific embodiments and the accompanying drawings. A person of ordinary skill in the art will have no problem understanding the features and effects of the invention from the disclosure of this specification and may implement or apply the invention from a different point of view by making various modifications and changes to the disclosed embodiments without departing from the spirit of the invention.

Figure 1:
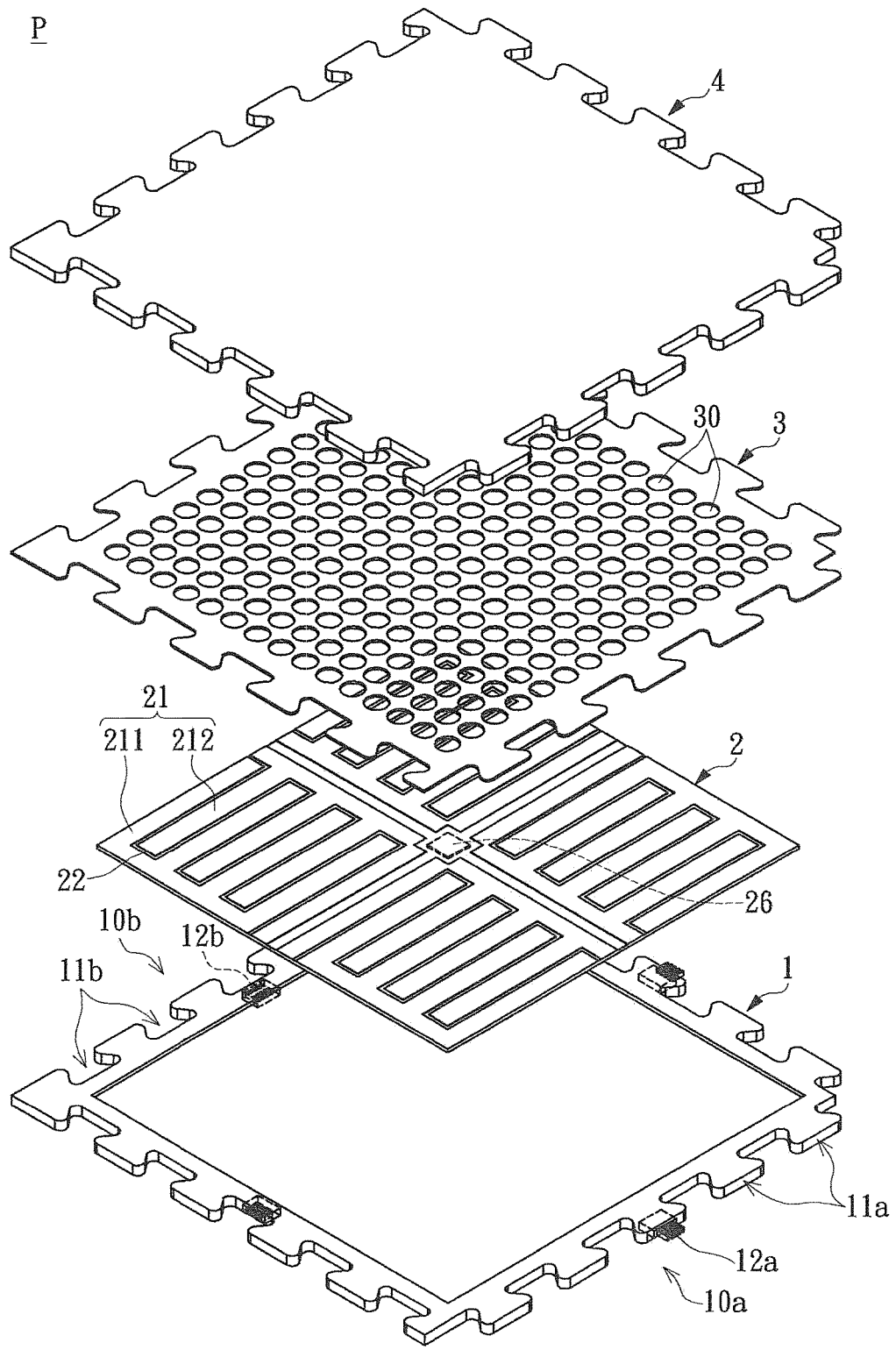
FIG. 1 is an exploded perspective view of a motion-sensing floor mat according to the present invention.
Figure 2:
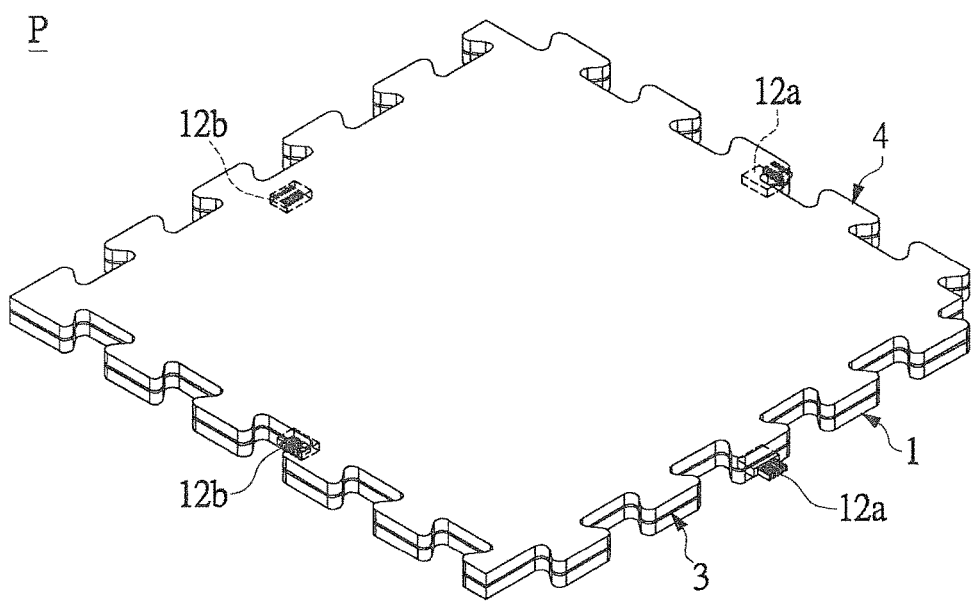
FIG. 2 is an assembled perspective view of the motion-sensing floor mat in FIG. 1.

Please refer to FIG. 1 and FIG. 2 respectively for an exploded perspective view and an assembled perspective view of the motion-sensing floor mat in a preferred embodiment of the present invention. In this preferred embodiment, the motion-sensing floor mat P includes, from bottom to top, a standardized base 1, a pressure-sensing layer 2, an insulating and isolating layer 3, and an elastic conductive layer 4. It is worth mentioning that, although the motion-sensing floor mat P in this preferred embodiment has a rectangular shape as one of its structural features, the motion-sensing floor mat P can, in principle, take any other suitable geometric shapes (e.g., a triangle, rhombus, or parallelogram) in order to meet the actual requirements of an indoor space. In addition, the motion-sensing floor mat P may have generally the same size as a commercially available plastic-made "interlocking floor mat". The present invention, in fact, has no limitation on size. The working principle of the motion-sensing floor mat P is similar to that of a membrane switch. Briefly stated, the insulating and isolating layer 3 isolates the overlying elastic conductive layer 4 from the underlying pressure-sensing layer 2 but allows contact between the elastic conductive layer 4 and the pressure-sensing layer 2 when an external force is applied to the motion-sensing floor mat P. The greater the pressure, the better the quality of contact between the elastic conductive layer 4 and the pressure-sensing layer 2.

In this preferred embodiment, the standardized base 1 has at least one pair of opposite assembly sides, depending on the shape of the standardized base 1. In FIG. 1, for example, there are a first assembly side 10*a* and a second assembly side 10*b*. The first assembly side 10*a* is configured to connect with the second assembly side 10*b* of another standardized base 1, and the second assembly side 10*b*, with the first assembly side 10*a* of yet another standardized base 1. Thus, at least two motion-sensing floor mats P can be joined together. In this preferred embodiment, the first assembly side 10*a* is provided with a plurality of first engaging portions 11*a* (e.g., engaging blocks), and the second assembly side 10*b* is provided with a plurality of second engaging portions 11*b* (e.g., engaging grooves). The second engaging portions 11b match the first engaging portions 11a in structure and form in order for the first engaging portions 11a to securely engage with the second engaging portions 11b of another motion-sensing floor mat P. One of the first engaging portions 11a of the first assembly side 10a is provided with a first information transmission module 12a, and one of the second engaging portions 11b of the second assembly side 10b is provided with a second information transmission module 12b. The first information transmission module 12a and the second information transmission module 12b correspond in position to each other (as shown in FIG. 2).

In this preferred embodiment, referring again to FIG. 1 and FIG. 2, the first and the second information transmission modules 12a and 12b are respectively a male electrical connector and a female electrical connector to be vertically connected with a corresponding male electrical connector by a pressing action. The present invention, however, has no limitation in this regard. In an alternative embodiment, for example, the first and the second information transmission modules 12a and 12b are respectively a male electrical connector and a female electrical connector to be vertically connected with a corresponding male electrical connector by magnetic attraction. A plurality of motion-sensing floor mats P can transmit information to one another through their respective first and second information transmission modules 12a and 12b.

Figure 3:
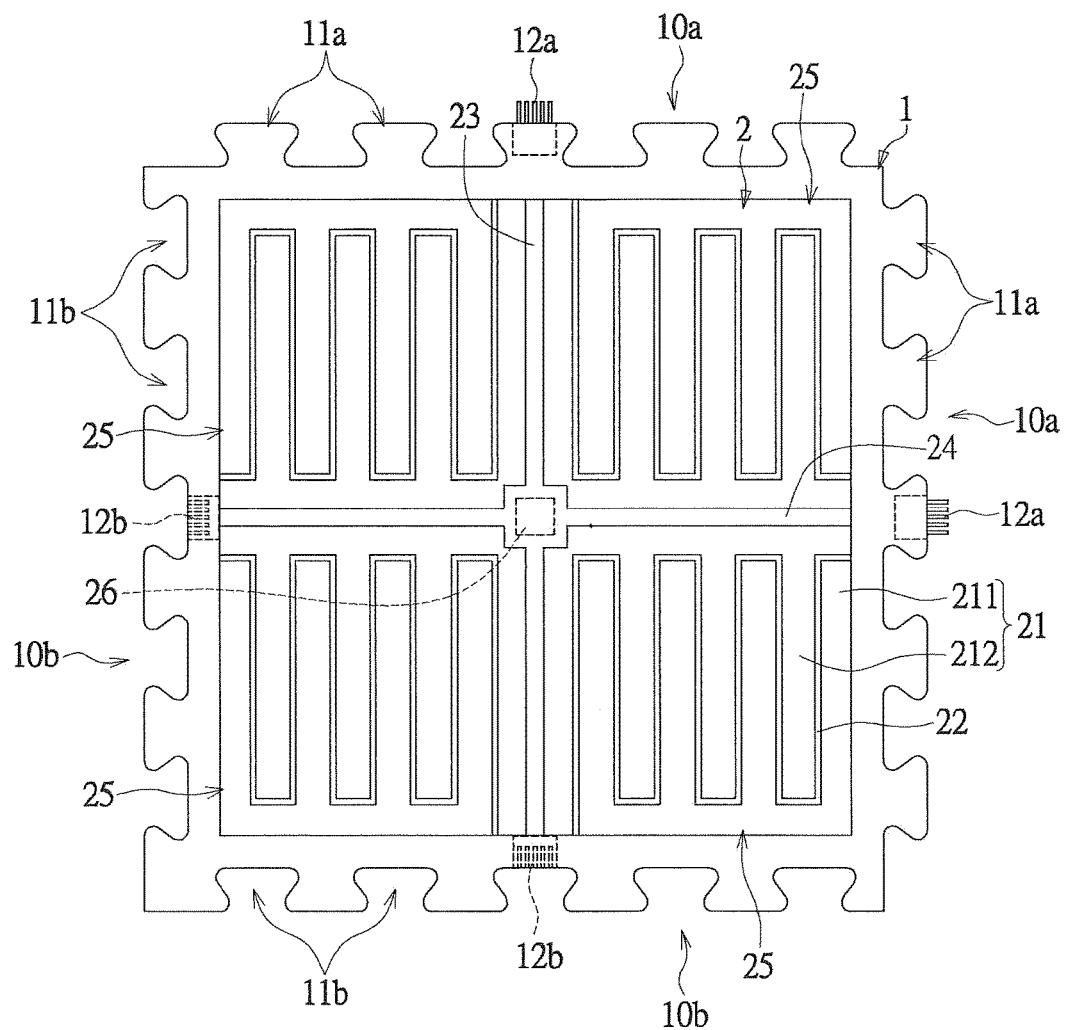
FIG. 3 schematically shows the standardized base and the pressure-sensing layer of the motion-sensing floor mat in FIG. 1.

As shown in FIGS. 1-3, the pressure-sensing layer 2 is provided on the standardized base 1 and has a plurality of sensing electrode assemblies 21. In this preferred embodiment, the standardized base 1 is formed with a receiving groove (not indicated in the drawings), whose configuration generally matches the peripheral contour of the pressure-sensing layer 2. The pressure-sensing layer 2 can be mounted in the receiving groove by any suitable assembly method such that the upper surface of the pressure-sensing layer 2 is flush with the upper surface of the standardized base 1. Each sensing electrode assembly 21 is composed of a first interdigital electrode 211 (an anode) and a second interdigital electrode 212 (a cathode), wherein the first interdigital electrode 211 and the second interdigital electrode 212 match each other in shape and jointly define a successively bent gap 22 therebetween. In FIG. 3, for example, each gap 22 is shaped in the contour of a crenellated wall, i.e., with consecutive square U-shaped bent sections. Under normal conditions, therefore, the first and the second interdigital electrodes 211 and 212 in each sensing electrode assembly 21 are not electrically connected to each other.

The layout of the sensing electrode assemblies 21 in the pressure-sensing layer 2 is detailed as follows. With continued reference to FIGS. 1~3, the pressure-sensing layer 2 is provided with at least one first-axial-direction wiring area 23 and at least one second-axial-direction wiring area 24. The first-axial-direction wiring area 23 is perpendicular to the second-axial-direction wiring area 24. The first- and the second-axial-direction wiring areas 23 and 24 jointly define a plurality of sensing areas 25, and each sensing electrode assembly 21 is provided in one of the sensing areas 25. The sensing electrode assemblies 21 are arranged in a regular pattern, in opposing pairs.

In order to apply the motion-sensing floor mat P to a domestic environment monitoring system, referring again to FIGS. 1-3, the pressure-sensing layer 2 is mounted with a control module 26 (e.g., a microprocessor) configured mainly to process pressure-sensing events. More specifically, when the motion-sensing floor mat P is subjected to pressure and generates a corresponding sensing signal, the control module 26 can relay the sensing signal to at least another adjoining motion-sensing floor mat P. In this preferred embodiment, the control module 26 is provided at the intersection of the first-axial-direction wiring area 23 and the second-axial-direction wiring area 24. The control module 26 is electrically connected not only to the sensing electrode assembly 21 in each sensing area 25, but also to the first and the second information transmission modules 12a and 12b through the first- and the second-axial-direction wiring areas 23 and 24. It should be pointed out that the foregoing shapes and locations of the first- and the second-axial-direction wiring areas 23 and 24 and the foregoing location of the control module 26 are only the preferred ones for the present invention and should not impose limitation on the design details of the invention. That is to say, the shapes and locations of the wiring areas and the location of the control module may vary as needed, provided that the plural sensing electrodes arranged in the floor mat can transmit information to the plural information transmission modules embedded in the periphery of the floor mat through the control module and the plural wiring areas.

Referring to FIGS. 1-5, the insulating and isolating layer 3 covers the pressure-sensing layer 2. In this preferred embodiment, the insulating and isolating layer 3 is a foam substrate layer of a specific thickness, ranging preferably from 1 cm to 4 cm, so as to provide temporary isolation that prevents the generation of erroneous contact signals when there is no pressure loading on the motion-sensing floor mat P. The insulating and isolating layer 3 is formed with a plurality of through holes 30, which may be circular, rectangular, or of other shapes. All or some of the through holes 30 are arranged along the gaps 22 of the sensing electrode assemblies 21, and the diameter of the through holes 30 must at least be larger than the width of the gaps 22. The elastic conductive layer 4 covers the insulating and isolating layer 3 and is equipotential. When implementing the present invention, the elastic conductive layer 4 may be made of fabric, air cushions, or other suitable elastic materials that are electrically conductive; the invention has no limitation in this regard.

Figure 6:
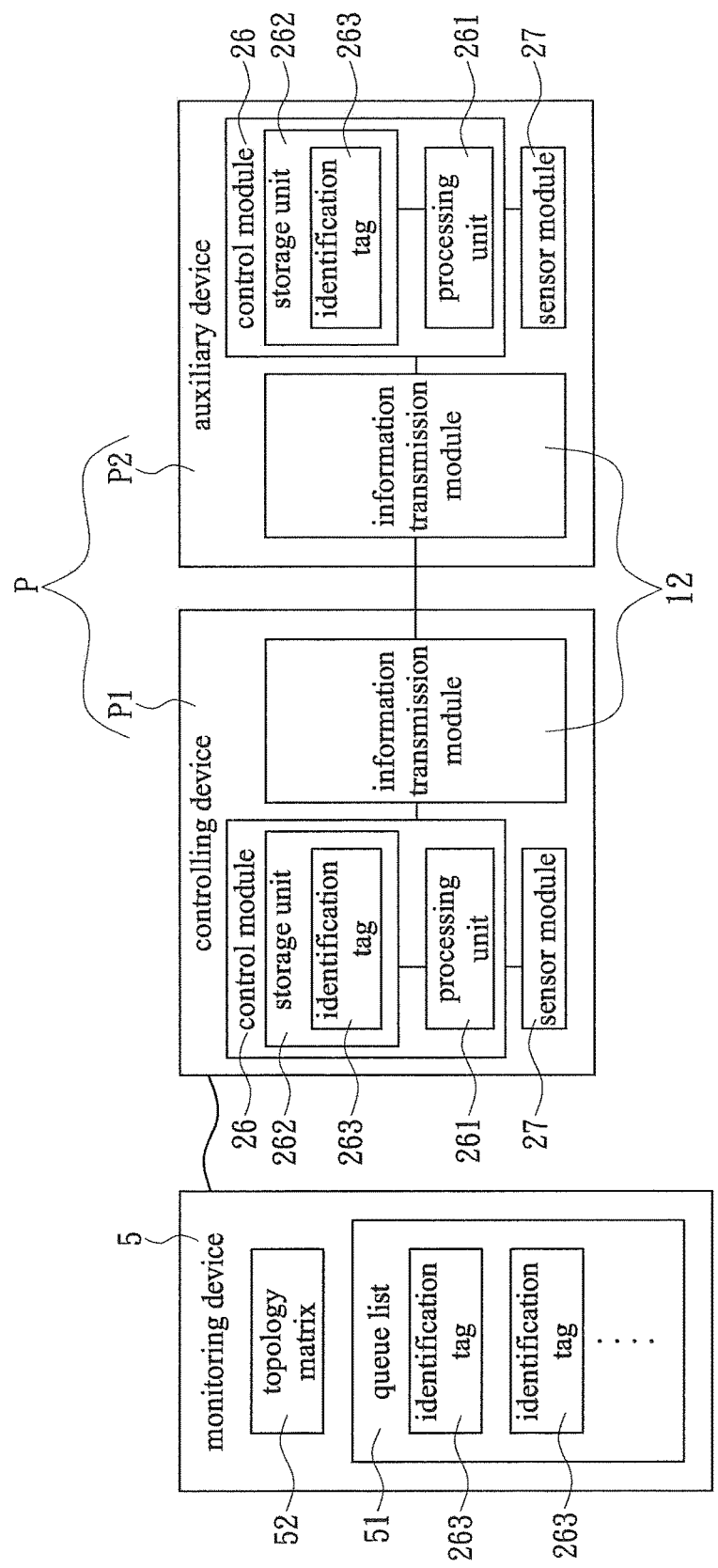
FIG. 6 schematically shows the hardware structure of a monitoring system according to the present invention.

According to the above, the motion-sensing floor mat P of the present invention has the hardware structure shown in FIG. 6, i.e., including the control module 26, a sensor module 27, and a plurality of information transmission modules 12 (namely the first and the second information transmission modules 12a and 12b). The control module 26 at least includes a processing unit 261 and a storage unit 262, wherein the storage unit 262 stores an identification tag 263. The processing unit 261 is electrically connected to the storage unit 262 and can read the identification tag 263. In practice, the control module 26 may be implemented as a single chip or multiple chips (i.e., with the processing unit 261 and the storage unit 262 being different chips). The sensor module 27 is composed of the pressure-sensing layer 2, the insulating and isolating layer 3, and the elastic conductive layer 4 in FIG. 1. When the motion-sensing floor mat P is subjected to pressure (e.g., being stepped on), the sensor module 27 generates a corresponding sensing signal and sends the sensing signal to the control module 26.

Figure 4:
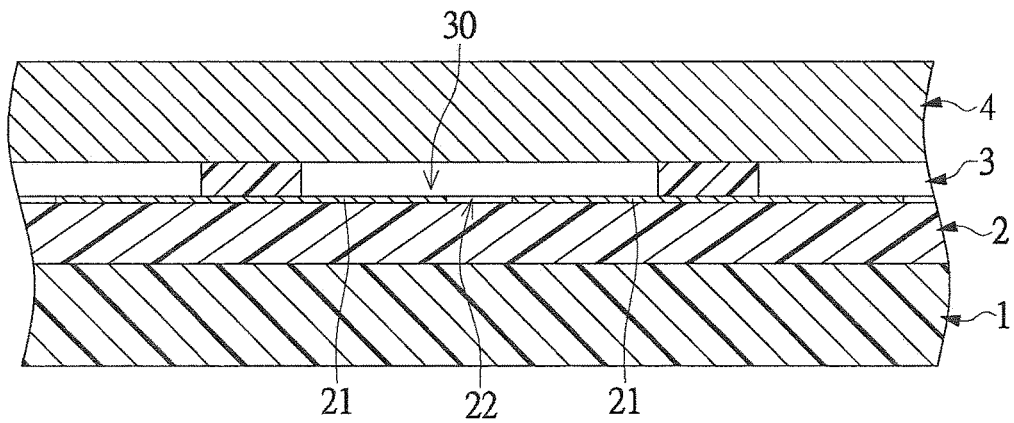
FIG. 4 schematically shows a state of use of the motion-sensing floor mat in FIG. 1.
Figure 5:
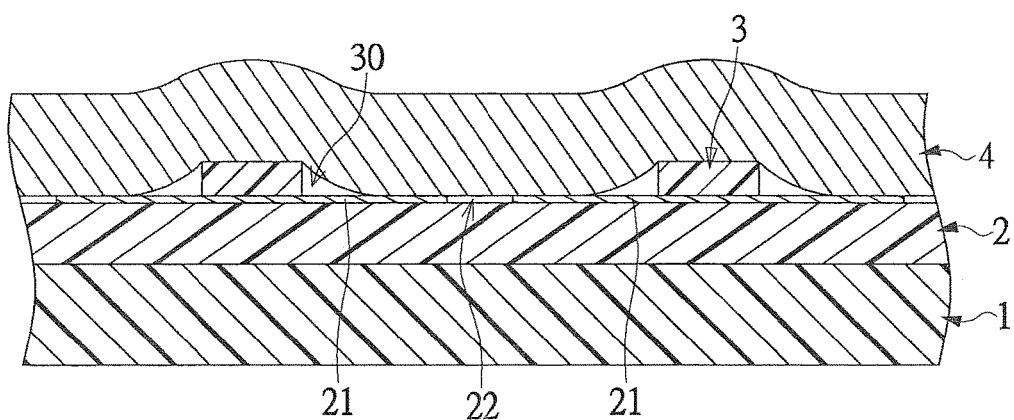
FIG. 5 schematically shows another state of use of the motion-sensing floor mat in FIG. 1.

The working principle of the motion-sensing floor mat P is detailed as follows with reference to FIGS. 1~6. To begin with, the elastic conductive layer 4, when in a state without pressure loading (as shown in FIG. 4), is not in contact with any of the sensing electrode assemblies 21 of the pressure-sensing layer 2 and therefore forms an open circuit. The total sensed resistance value obtained by the control module 26 in this state approaches infinity. When the elastic conductive layer 4 is subsequently pressed and deformed by an external force (i.e., in a state with pressure loading, as shown in FIG. 5), certain portions of the elastic conductive layer 4 are brought into contact with the corresponding sensing electrode assembly/assemblies 21 through the corresponding through holes 30 in the insulating and isolating layer 3 to form a closed circuit. In this state, the total sensed resistance value obtained by the control module 26 should be a value (i.e., a sensing signal) generated by series/parallel connection of the sensed resistance of the elastic conductive layer 4 and the sensed resistance of the sensing electrode assembly/assemblies 21. Please note that the total sensed resistance value is a function of the number of contact point(s) between the elastic conductive layer 4 and the corresponding sensing electrode assembly/assemblies 21 and the tightness of the contact. In other words, the total sensed resistance value will vary with the magnitude of the pressure loading and the size of the loaded area, allowing the motion (e.g., standing or being seated) of an elderly person or person with mobility impairment to be identified.

Figure 7:
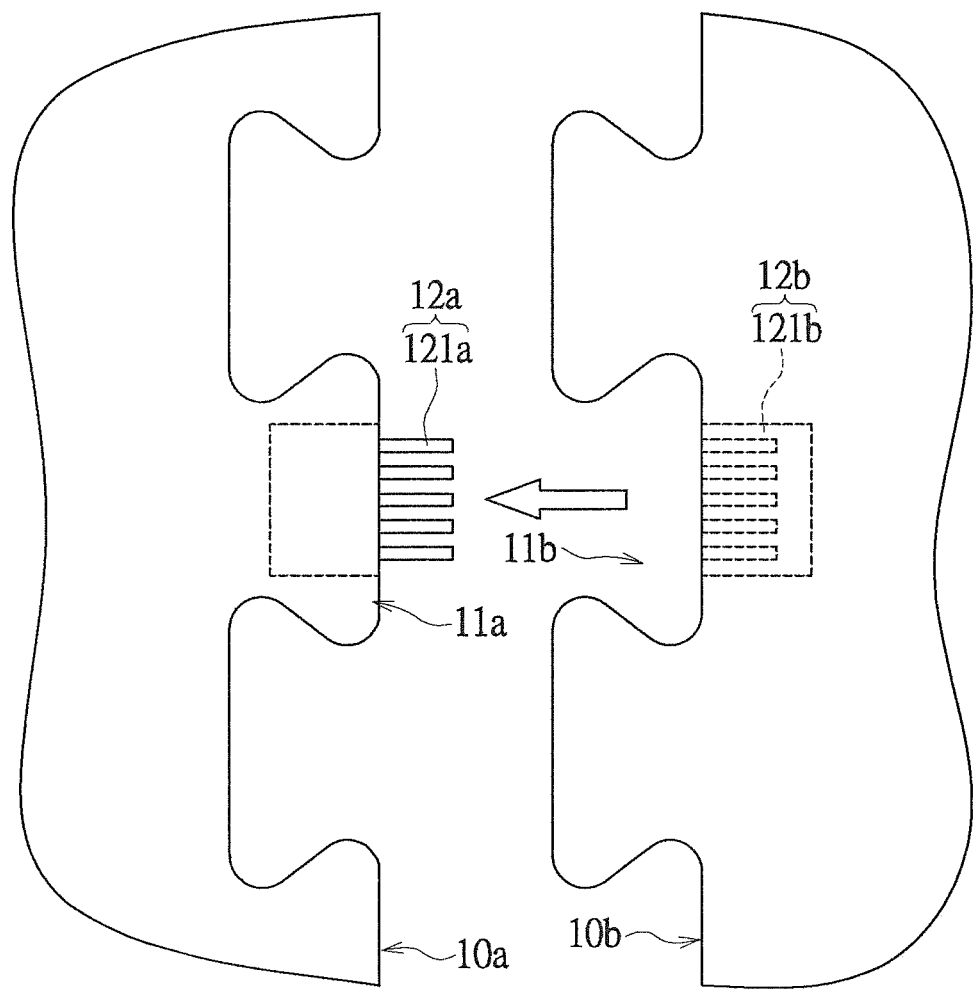
FIG. 7 schematically shows how two motion-sensing floor mats according to the present invention are put together.

The following paragraphs describe a monitoring system formed by the motion-sensing floor mat P. Referring to FIG. 6 in conjunction with FIG. 1 and FIG. 7, the monitoring system includes a plurality of motion-sensing floor mats P and a monitoring device 5 (e.g., a computer), wherein the motion-sensing floor mats P have the same specifications and are joined together to form a motion-sensing floor mat assembly. More specifically, the second engaging portions 11*b* of the second assembly side 10*b* of each motion-sensing floor mat P can be securely engaged, in a downward direction, with the first engaging portions 11*a* of the first assembly side 10*a* of another motion-sensing floor mat P such that the corresponding second and first information transmission modules 12*b* and 12*a* of the motion-sensing floor mats P are physically and electrically connected to each other. The motion-sensing floor mats P can be assembled in different configurations, such as the one shown in FIG. 8. In this preferred embodiment, each first information transmission module 12*a* is provided with a row of signal output terminals 121*a* protruding from the corresponding first engaging portion 11*a*. Likewise, each second information transmission module 12*b* is provided with a row of terminal grooves 121*b* that are exposed on the bottom of the corresponding standardized base 1, match the row of signal output terminals 121*a* respectively, and are configured to connect vertically and respectively with the row of signal output terminals 121*a* of a corresponding first information transmission module 12*a*.

To facilitate description of the working principle of the monitoring system, both the first information transmission modules 12*a* and the second information transmission modules 12*b* are hereinafter referred to as the information transmission modules 12. In this preferred embodiment, with continued reference to FIG. 6 and FIG. 8, each motion-sensing floor mat P is provided with four information transmission modules 12 on its four sides respectively, and each information transmission module 12 corresponds to certain position information (e.g., forward side, rearward side, left side, or right side). In this preferred embodiment, each two adjacent motion-sensing floor mats P joined together can transmit information to each other through the corresponding connected information transmission modules 12. That is to say, when plural motion-sensing floor mats P are joined together and all the corresponding information transmission modules 12 are connected in pairs, the processing unit 261 of any motion-sensing floor mat P can, after reading the identification tag 263 of the motion-sensing floor mat P or receiving a sensing signal, send the identification tag 263 or the sensing signal to another motion-sensing floor mat P through the corresponding information transmission modules 12 of the two motion-sensing floor mats P.

Referring again to FIG. 6 and FIG. 8, the monitoring device 5 stores a queue list 51 and a topology matrix 52 and is electrically connected to one of the motion-sensing floor mats P. The motion-sensing floor mat P electrically connected to the monitoring device 5 serves as a controlling device P1 while all the other motion-sensing floor mats P, which are connected to the controlling device P1 either directly or indirectly, serve as auxiliary devices P2. The monitoring device 5 in the present invention is configured for driving the control modules 26 of the motion-sensing floor mats P to detect their respective information transmission modules 12; establishing the queue list 51 in stages, based on the detection results, wherein the queue list 51 corresponds to the motion-sensing floor mats P detected and is established by means of the breadth-first search (BFS) algorithm and the first-in first-out method; and gradually establishing the topology matrix 52 according to the queue list 51, wherein the topology matrix 52 is composed of all the motion-sensing floor mats P detected and enables the monitoring device 5 to rapidly locate any motion-sensing floor mat P that has sent out a sensing signal.

Figure 9:
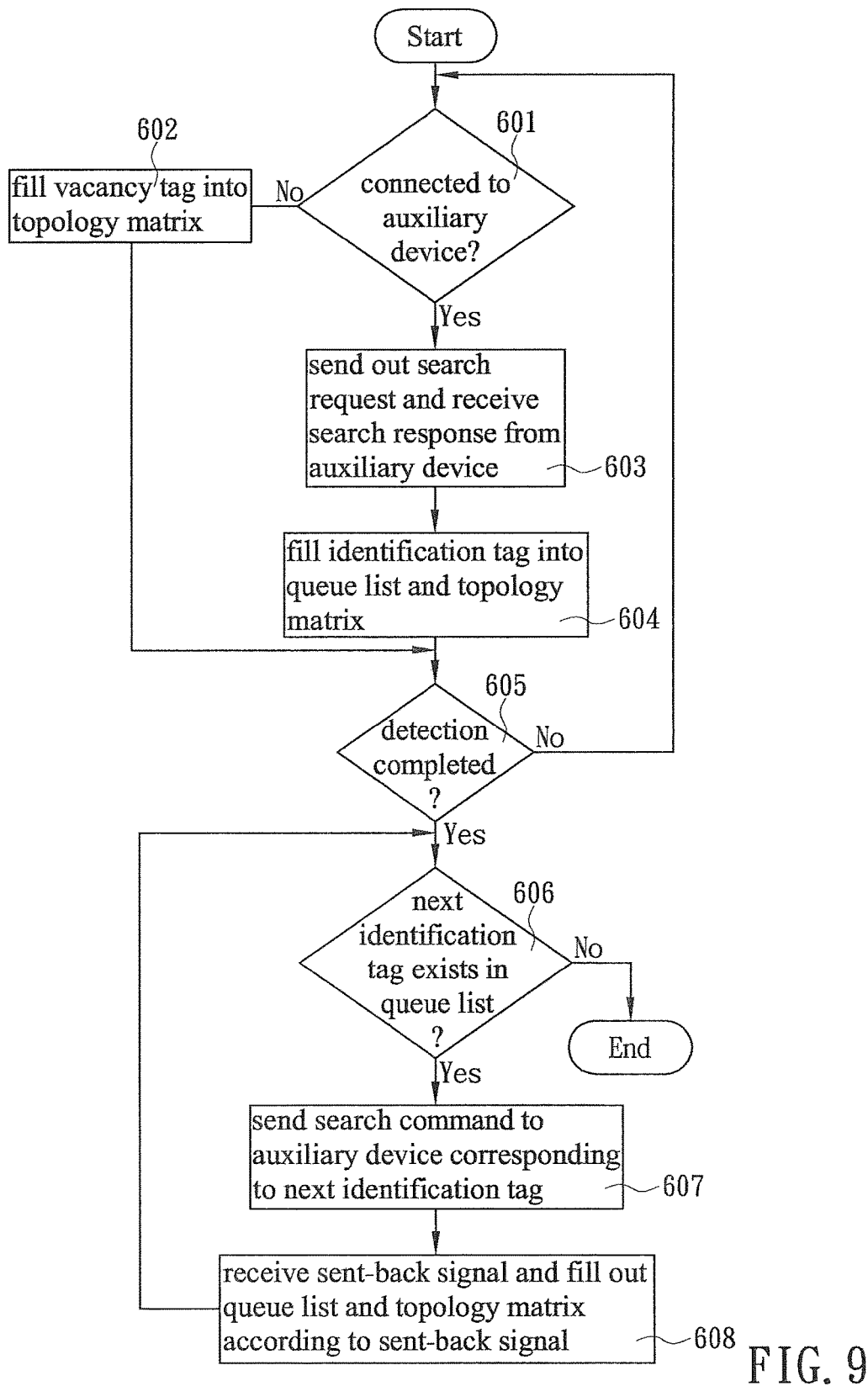
FIG. 9 is a flowchart showing the major steps of the present invention.

The process flow, or more particularly a topological algorithm, of the present invention is now detailed with reference to the flowchart in FIG. 9 and the reference numerals in FIG. 6. This topological algorithm includes the following steps to be performed by the monitoring device 5:

(601) Drive the control module 26 of the controlling device P1 to detect the information transmission modules 12 of the controlling device P1 sequentially, in order to determine whether each of the information transmission modules 12 of the controlling device P1 is connected to an information transmission module 12 of an adjacent auxiliary device P2. If no, step (602) is performed, or if yes, step (603) is performed.

(602) Based on the position information of the information transmission module 12 detected, fill the corresponding position in the topology matrix 52 with a vacancy tag (e.g., the code 0). Continue to step (605).

(603) Send a search request to the adjacent auxiliary device P2 through the information transmission module 12 detected, in order for the auxiliary device P2 to send back a search response according to the search request after receiving the search request, wherein the search response includes the identification tag 263 of the auxiliary device P2 and the position information of the information transmission module 12 having received the search request. Continue to step (604).

(604) After receiving each search response, store the identification tag 263 in the search response into the queue list 51 in order, and based on the position information in the search response, fill the corresponding position in the topology matrix 52 with the identification tag 263. Continue to step (605).

(605) Determine whether all the information transmission modules 12 of the controlling device P1 have been detected. If no, return to step (601); if yes, continue to step (606).

(606) Determine whether a next identification tag 263 exists in the queue list 51. If yes, continue to step (607); otherwise, end the process flow.

(607) Read the next identification tag 263 in the queue list 51, and send a search command to the auxiliary device P2 corresponding to that identification tag 263, in order for the auxiliary device P2 to respond to the search command by detecting its information transmission modules 12 sequentially and either sending back a vacancy response corresponding to the position information of the information transmission module 12 detected or sending a search request through the information transmission module 12 detected to the adjacent auxiliary device P2 and then sending back a search response. After detecting all its information transmission modules 12, the auxiliary device P2 sends an ending response to the monitoring device 5 and enters a no-responding state, in which the auxiliary device P2 will not send out any search response when subsequently receiving a search request from another auxiliary device P2.

(608) When receiving a vacancy response, refer to the position information of the information transmission module 12 in the vacancy response and fill the corresponding position in the topology matrix 52 with a vacancy tag. When receiving a search response, store the identification tag 263 in the search response into the queue list 51 in order, refer to the position information in the research response, and fill the corresponding position in the topology matrix 52 with the identification tag 263. Return to step (606) when receiving the ending response.

Figure 8:
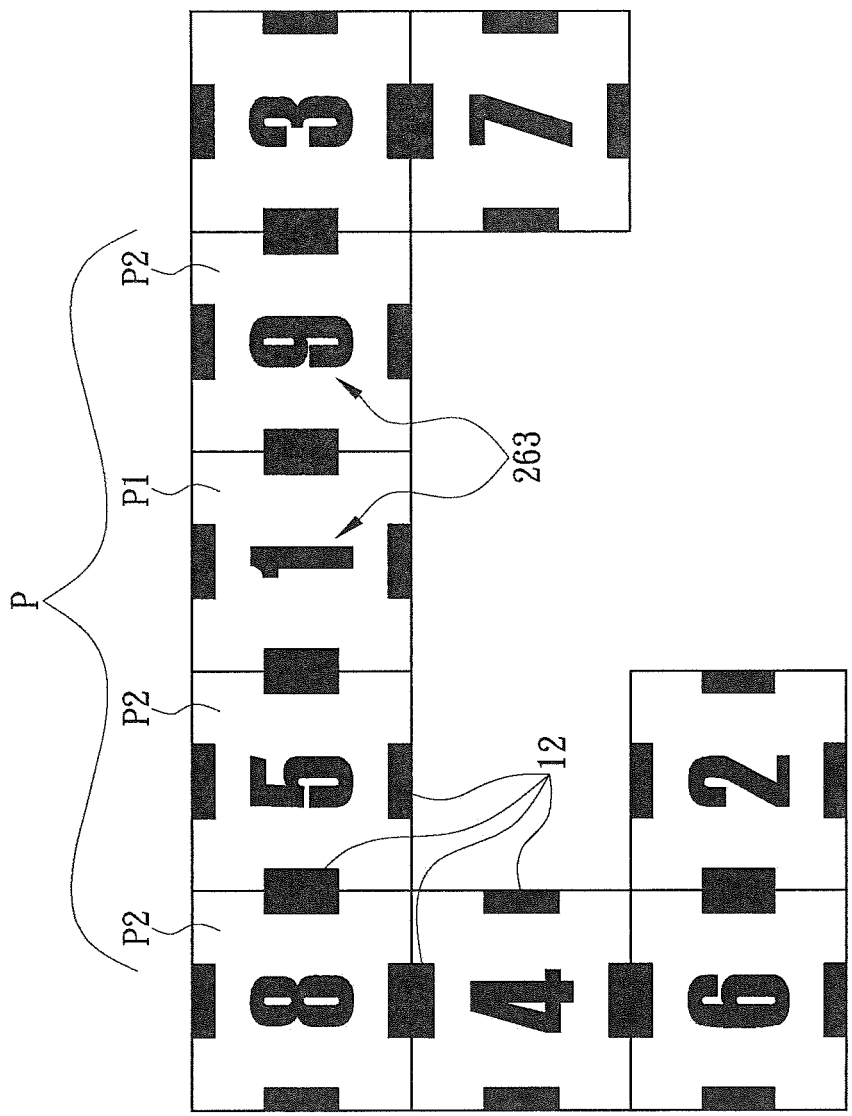
FIG. 8 schematically shows a motion-sensing floor mat assembly according to the present invention.
Figure 10:
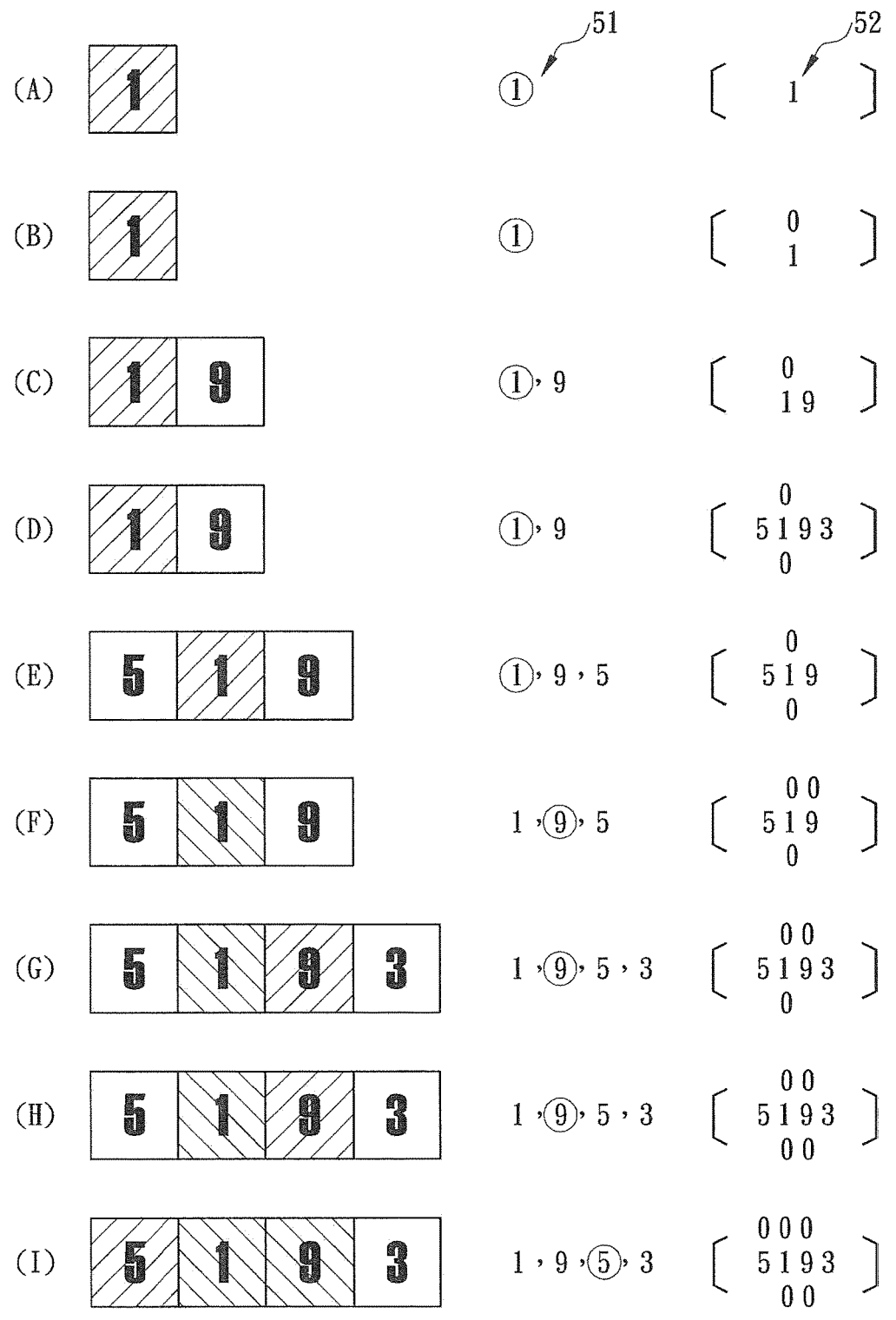

To enable more intuitive understanding of the topological algorithm of the present invention (i.e., the steps of establishing the queue list 51 and the topology matrix 52 using the BFS algorithm and the first-in first-out method), the following example is provided, with reference to the schematic drawing in FIG. 10 as well as the reference numerals in FIG. 6 and the joining arrangement of the motion-sensing floor mats P in FIG. 8. In FIG. 10, each motion-sensing floor mat P in the left column that is marked with lines extending "from the upper right corner to the lower left corner" is in the process of detecting its information transmission modules 12, and so is the motion-sensing floor mat P corresponding to each circled identification tag 263 in the middle column. Each motion-sensing floor mat P in the left column in FIG. 10 that is marked with lines extending "from the upper left corner to the lower right corner" is in the no-responding state. In the first step, the monitoring device 5 stores the identification tag 263 of the controlling device P1 (which in this example is the motion-sensing floor mat P with the identification tag 263 #1) into the queue list 51 and fills the corresponding position in the topology matrix 52 with the identification tag 263 of the controlling device P1. Then, the monitoring device 5 drives the control module 26 of the controlling device P1 to detect (in an order starting from the forward side, followed sequentially by the right side, the rearward side, and the left side) all the auxiliary devices P2, if any, joined to the controlling device P1. If no auxiliary device P2 is detected at a certain side, the corresponding position in the topology matrix 52 is filled with the code 0. But if an auxiliary device P2 is detected at a certain side, the identification tag 263 of the auxiliary device P2 detected is recorded in the queue list 51 in order and also filled into the corresponding position in the topology matrix 52.

When the controlling device P1 completes detecting all its information transmission modules 12, the monitoring device 5 reads the next identification tag 263 in the queue list 51 and drives the auxiliary device P2 corresponding to the identification tag 263 (which in this example is the motion-sensing floor mat P with the identification tag 263 #9), in order for the control module 26 of this auxiliary device P2 to detect (in an order starting from the forward side, followed sequentially by the right side, the rearward side, and the left side) all the auxiliary devices P2, if any, joined to this auxiliary device P2. When this auxiliary device P2 completes detecting all its information transmission modules 12, the monitoring device 5 goes on to read the following identification tags 263 in the queue list 51 (which in this example are the identification tags 263 #5, #3, #8, #7, #4, #6, and #2, in that order) one after another. The monitoring device 5 sequentially drives the corresponding auxiliary devices P2 to detect their respective information transmission modules 12 until all the auxiliary devices P2 corresponding to the identification tags 263 in the queue list 51 have completed detection.

Thus, the relative positions of the motion-sensing floor mats P can be obtained through the topological algorithm, and when any of the motion-sensing floor mats P is under pressure and generates a sensing signal, the monitoring device 5 can refer to the topology matrix 52 to obtain the actual location of the motion-sensing floor mat P generating the sensing signal. In other words, should an elderly person or child accidentally fall on one of the motion-sensing floor mats P, the specific location of the fall can be instantly known through the sensing signal.

The present invention has at least the following advantages over its prior art counterparts in sensing human body motion in a domestic environment:

1. The motion-sensing floor mat of the present invention integrates a motion-sensing technique into a floor mat and uses a standardized base with vertically connectable information transmission modules. When applied to a domestic monitoring system, a plurality of such floor mats can be freely joined together to meet the actual requirements of an indoor space, allowing the interaction between a person needing care (e.g., an elderly person, a person with mobility impairment, or a child) and the indoor space to be monitored continuously by a non-conscious sensing method. Consequently, the motion of the person needing care can be known with precision, and any necessary medical care, provided as soon as possible.

2. The motion-sensing floor mat of the present invention is highly accurate and sensitive in signal detection thanks to its main sensing unit, which includes the porous insulating and isolating layer and the underlying pressure-sensing layer, and to the through holes in the insulating and isolating layer, which are arranged along the successively bent gaps of the sensing electrode assemblies in the pressure-sensing layer.

3. The monitoring system of the present invention does not monitor a person's body motion in a proactive or invasive manner and therefore will not interfere with the person's daily life or cause much, if any, metal stress on the person being monitored.

4. The motion-sensing floor mat of the present invention features great convenience of use because a user can join a plurality of such floor mats together arbitrarily, without having to arrange them in a particular order; nevertheless, the monitoring device can obtain the location of each motion-sensing floor mat accurately.

While the invention herein disclosed has been described by means of specific embodiments, numerous modifications and variations could be made thereto by those skilled in the art without departing from the scope of the invention set forth in the claims.

What is claimed is:

1. A motion-sensing floor mat, configured to join with at least one other said motion-sensing floor mat and be electrically connected to a monitoring device in order to form a monitoring system, wherein the monitoring device detects the at least one other motion-sensing floor mat, stores a queue list and a topology matrix, and uses a topological algorithm to store an identification tag of each said detected motion-sensing floor mat into the queue list in order of detection, to gradually establish the topology matrix for the detected motion-sensing floor mats, and to thereby obtain relative positions of the detected motion-sensing floor mats, the motion-sensing floor mat comprising:
- a standardized base having a first assembly side and a second assembly side, wherein the first assembly side and the second assembly side correspond to each other, the first assembly side is provided with a plurality of first engaging portions, one of the first engaging portions is provided with a first information transmission module, the second assembly side is provided with a plurality of second engaging portions, one of the second engaging portions is provided with a second information transmission module, and the first information transmission module and the second information transmission module correspond to each other;
- a pressure-sensing layer provided on the standardized base and having a plurality of sensing electrode assemblies, wherein the sensing electrode assemblies are electrically connected to the first information transmission module and the second information transmission module, and each of the sensing electrode assemblies is provided with a successively bent gap;
- an insulating and isolating layer covering the pressure-sensing layer and having a plurality of through holes, wherein some of the through holes are sequentially arranged along the gaps of the sensing electrode assemblies; and
- an elastic conductive layer covering the insulating and isolating layer such that, when a portion of the elastic conductive layer is compressed by an external force, the compressed portion of the elastic conductive layer is brought into contact with the pressure-sensing layer through corresponding ones of the through holes.

2. The motion-sensing floor mat of claim 1, wherein the pressure-sensing layer is provided with at least one first-axial-direction wiring area and at least one second-axial-direction wiring area, the first-axial-direction wiring area is perpendicular to the second-axial-direction wiring area to form a plurality of sensing areas, and the sensing electrode assemblies are provided in the sensing areas respectively.

3. The motion-sensing floor mat of claim 2, wherein each of the sensing electrode assemblies comprises a first interdigital electrode and a second interdigital electrode matching the first interdigital electrode in shape such that said successively bent gap is formed therebetween.

4. The motion-sensing floor mat of claim 2, wherein the pressure-sensing layer further comprises a control module; and the control module has the identification tag of the motion-sensing floor mat, is located at an intersection of the first-axial-direction wiring area and the second-axial-direction wiring area, is electrically connected to the sensing electrode assemblies, and is electrically connected to the first information transmission module and the second information transmission module through the first-axial-direction wiring area or the second-axial-direction wiring area.

5. The motion-sensing floor mat of claim 3, wherein the pressure-sensing layer further comprises a control module; and the control module has the identification tag of the motion-sensing floor mat, is located at an intersection of the first-axial-direction wiring area and the second-axial-direction wiring area, is electrically connected to the sensing electrode assemblies, and is electrically connected to the first information transmission module and the second information transmission module through the first-axial-direction wiring area or the second-axial-direction wiring area.

6. The motion-sensing floor mat of claim 4, wherein the first information transmission module is provided with a row of signal output terminals protruding from a corresponding one of the first engaging portions, and the second information transmission module is provided with a row of terminal grooves matching the row of signal output terminals respectively so as to connect vertically with a corresponding said row of signal output terminals respectively.

7. The motion-sensing floor mat of claim 5, wherein the first information transmission module is provided with a row of signal output terminals protruding from a corresponding one of the first engaging portions, and the second information transmission module is provided with a row of terminal grooves matching the row of signal output terminals respectively so as to connect vertically with a corresponding said row of signal output terminals respectively.

8. A motion-sensing floor mat assembly, configured to be electrically connected to a monitoring device in order to form a monitoring system, wherein the monitoring device senses human body motion by receiving and analyzing a sensing signal, the motion-sensing floor mat assembly comprising:
- two motion-sensing floor mats joined to each other, wherein one of the motion-sensing floor mats is connected to the monitoring device; the monitoring device detects the at least one other motion-sensing floor mat, stores a queue list and a topology matrix, and uses a topological algorithm to store an identification tag of each said detected motion-sensing floor mat into the queue list in order of detection, to gradually establish the topology matrix for the detected motion-sensing floor mats, and to thereby obtain relative positions of the detected motion-sensing floor mats; and each of the motion-sensing floor mats comprises:
- a standardized base having a first assembly side and a second assembly side, wherein the first assembly side and the second assembly side correspond to each other, the first assembly side is provided with a plurality of first engaging portions, one of the first engaging portions is provided with a first information transmission module, the second assembly side is provided with a plurality of second engaging portions, one of the second engaging portions is provided with a second information transmission module, and the first information transmission module and the second information transmission module correspond to each other;
- a pressure-sensing layer provided on the standardized base and having a control module and a plurality of sensing electrode assemblies, wherein the control module has the identification tag of said each of the motion-sensing floor mats and is separately electrically connected to the sensing electrode assemblies, the first information transmission module, and the second information transmission module; and each of the sensing electrode assemblies is provided with a successively bent gap;
- an insulating and isolating layer covering the pressure-sensing layer and having a plurality of through holes, wherein some of the through holes are sequentially arranged along the gaps of the sensing electrode assemblies; and
- an elastic conductive layer covering the insulating and isolating layer such that, when a portion of the elastic conductive layer is compressed by an external force, the compressed portion of the elastic conductive layer is brought into contact with the pressure-sensing layer through corresponding ones of the through holes;

wherein when the two motion-sensing floor mats are joined to each other, the first engaging portions of one of the motion-sensing floor mats are securely engaged with the second engaging portions of the other of the motion-sensing floor mats, and the first information transmission module of the one of the motion-sensing floor mats is connected with the second information transmission module of the other of the motion-sensing floor mats.

9. The motion-sensing floor mat assembly of claim 8, wherein each of the motion-sensing floor mats is characterized in that the pressure-sensing layer is provided with at least one first-axial-direction wiring area and at least one second-axial-direction wiring area, the first-axial-direction wiring area is perpendicular to the second-axial-direction wiring area to form a plurality of sensing areas, and the sensing electrode assemblies are provided in the sensing areas respectively.

10. The motion-sensing floor mat assembly of claim 8, wherein each of the motion-sensing floor mats is characterized in that:

each of the sensing electrode assemblies comprises a first interdigital electrode and a second interdigital electrode matching the first interdigital electrode in shape such that said successively bent gap is formed therebetween.

11. The motion-sensing floor mat assembly of claim 8, wherein each of the motion-sensing floor mats is characterized in that:

the control module is located at an intersection of the first-axial-direction wiring area and the second-axial-direction wiring area and is electrically connected to the first information transmission module and the second information transmission module through the first-axial-direction wiring area or the second-axial-direction wiring area.

12. The motion-sensing floor mat assembly of claim 10, wherein each of the motion-sensing floor mats is characterized in that:

the control module is located at an intersection of the first-axial-direction wiring area and the second-axial-direction wiring area and is electrically connected to the first information transmission module and the second information transmission module through the first-axial-direction wiring area or the second-axial-direction wiring area.

13. The motion-sensing floor mat assembly of claim 11, wherein each of the motion-sensing floor mats is characterized in that:

the first information transmission module is provided with a row of signal output terminals protruding from a corresponding one of the first engaging portions, and the second information transmission module is provided with a row of terminal grooves matching the row of signal output terminals respectively so as to connect vertically with a corresponding said row of signal output terminals respectively.

14. The motion-sensing floor mat assembly of claim 12, wherein each of the motion-sensing floor mats is characterized in that:

the first information transmission module is provided with a row of signal output terminals protruding from a corresponding one of the first engaging portions, and the second information transmission module is provided with a row of terminal grooves matching the row of signal output terminals respectively so as to connect vertically with a corresponding said row of signal output terminals respectively.

15. A monitoring system with motion-sensing floor mats, comprising:

a plurality of said motion-sensing floor mats joined together, each provided with a control module, a sensor module, and a plurality of information transmission modules, wherein in each of the motion-sensing floor mats, the control module is separately electrically connected to the sensor module and the information transmission modules and has an identification tag of said each of the motion-sensing floor mats; the sensor module of any one of the motion-sensing floor mats that is under pressure generates a sensing signal, and the control module of the motion-sensing floor mat that is under pressure receives the sensing signal and sends a respective identification tag or the sensing signal to an adjacent said motion-sensing floor mat through corresponding ones of the information transmission modules of the motion-sensing floor that is under pressure and the adjacent said motion-sensing floor mat; the information transmission modules of each of the motion-sensing floor mats are provided along a periphery of said each of the motion-sensing floor mats and each correspond to predetermined position information; and any two adjacent said motion-sensing floor mats joined together are able to transmit information to each other through corresponding connected ones of the information transmission modules of the two motion-sensing floor mats; and a monitoring device storing a queue list and a topology matrix and electrically connected to one of the motion-sensing floor mats such that the motion-sensing floor mat electrically connected to the monitoring device serves as a controlling device while each other motion-sensing floor mat that is directly or indirectly connected to the controlling device serves as an auxiliary device, wherein the monitoring device uses a topological algorithm to store the identification tag of each said detected motion-sensing floor mat into the queue list in order, to gradually establish the topology matrix for the detected motion-sensing floor mats, and to thereby obtain relative positions of the detected motion-sensing floor mats; and when any of the motion-sensing floor mats is under pressure and generates a respective said sensing signal, the topology matrix enables the monitoring device to determine an actual position of the motion-sensing floor mat generating the sensing signal.

16. The monitoring system of claim 15, wherein the topological algorithm comprises the steps, to be performed by the monitoring device, of:

driving the control module of the controlling device to sequentially detect the information transmission modules of the controlling device for connection with said information transmission module of an adjacent said auxiliary device;

filling a vacancy tag into a position in the topology matrix that corresponds to the position information of said information transmission module of the controlling device if the information transmission module is not connected with said information transmission module of an adjacent said auxiliary device;

sending a search request to an adjacent said auxiliary device through said information transmission module of the controlling device and said information transmission module of the adjacent auxiliary device if the information transmission module of the controlling device is connected with the information transmission module of the adjacent auxiliary device, in order for the adjacent auxiliary device to send back a search response according to the search request after receiving the search request, wherein the search response comprises the identification tag of the adjacent auxiliary device and the position information of the information transmission module having received the search request; and storing the identification tag in each said search response received into the queue list in order, and filling the identification tag in each said search response received into a position in the topology matrix that corresponds to the position information in each said search response received.

17. The monitoring system of claim 15, wherein the topological algorithm further comprises the steps, to be performed by the monitoring device, of:

driving the control module of the controlling device to detect another said information transmission module of the controlling device;

reading a next said identification tag in the queue list if all the information transmission modules of the controlling device have been detected, and driving the auxiliary device corresponding to the next identification tag through the controlling device; and terminating the topological algorithm if the next identification tag does not exist.

18. The monitoring system of claim 17, wherein the topological algorithm further comprises the step, to be performed by the monitoring device, of:

sending a search command to the auxiliary device corresponding to the next identification tag, in order for the auxiliary device corresponding to the next identification tag to sequentially detect the information transmission modules thereof according to the search command and either send back a vacancy response corresponding to the position information of said information transmission module detected or send said search request to an adjacent said auxiliary device through the information transmission module detected and then send back said search response.

19. The monitoring system of claim 18, wherein each said auxiliary device having detected all the information transmission modules thereof sends back an ending response, enters a no-responding state, and therefore no longer sends back any said search response when subsequently receiving said search request from another said auxiliary device.

20. The monitoring system of claim 19, wherein the topological algorithm further comprises the steps, to be performed by the monitoring device, of:

filling a vacancy tag into a position in the topology matrix that corresponds to the position information of the information transmission module in each said vacancy response received; or storing the identification tag in each said search response received into the queue list in order, and filling the identification tag in each said search response received into a position in the topology matrix that corresponds to the position information in each said search response received;

reading a next said identification tag in the queue list when receiving the ending response, and driving the auxiliary device corresponding to the next identification tag through the controlling device; and terminating the topological algorithm if the next identification tag does not exist.

21. The monitoring system of claim 20, wherein each said control module comprises a processing unit and a storage unit, the storage unit storing a corresponding said identification tag, the processing unit being electrically connected to the storage unit in order to read the corresponding identification tag.

22. The monitoring system of claim 15, wherein each said sensor module comprises:

a pressure-sensing layer provided in a corresponding said motion-sensing floor mat and having a corresponding said control module and a plurality of sensing electrode assemblies, wherein the corresponding control module is electrically connected to the sensing electrode assemblies, the sensing electrode assemblies are electrically connected to each of the information transmission modules of the corresponding motion-sensing floor mat such that the corresponding control module is electrically connected to each of the information transmission modules of the corresponding motion-sensing floor mat through the sensing electrode assemblies, and each of the sensing electrode assemblies is provided with a successively bent gap;

an insulating and isolating layer covering the pressure-sensing layer and having a plurality of through holes, wherein some of the through holes are sequentially arranged along the gaps of the sensing electrode assemblies; and an elastic conductive layer covering the insulating and isolating layer;

wherein when a portion of the elastic conductive layer is compressed by an external force, the compressed portion of the elastic conductive layer is brought into contact with the pressure-sensing layer through corresponding ones of the through holes such that the pressure-sensing layer generates said sensing signal and sends the sensing signal to the corresponding control module.

23. The monitoring system of claim 16, wherein each said sensor module comprises:

a pressure-sensing layer provided in a corresponding said motion-sensing floor mat and having a corresponding said control module and a plurality of sensing electrode assemblies, wherein the corresponding control module is electrically connected to the sensing electrode assemblies, the sensing electrode assemblies are electrically connected to each of the information transmission modules of the corresponding motion-sensing floor mat such that the corresponding control module is electrically connected to each of the information transmission modules of the corresponding motion-sensing floor mat through the sensing electrode assemblies, and each of the sensing electrode assemblies is provided with a successively bent gap;

an insulating and isolating layer covering the pressure-sensing layer and having a plurality of through holes, wherein some of the through holes are sequentially arranged along the gaps of the sensing electrode assemblies; and an elastic conductive layer covering the insulating and isolating layer;

wherein when a portion of the elastic conductive layer is compressed by an external force, the compressed portion of the elastic conductive layer is brought into contact with the pressure-sensing layer through corresponding ones of the through holes such that the pressure-sensing layer generates said sensing signal and sends the sensing signal to the corresponding control module.

24. The monitoring system of claim 17, wherein each said sensor module comprises:
- a pressure-sensing layer provided in a corresponding said motion-sensing floor mat and having a corresponding said control module and a plurality of sensing electrode assemblies, wherein the corresponding control module is electrically connected to the sensing electrode assemblies, the sensing electrode assemblies are electrically connected to each of the information transmission modules of the corresponding motion-sensing floor mat such that the corresponding control module is electrically connected to each of the information transmission modules of the corresponding motion-sensing floor mat through the sensing electrode assemblies, and each of the sensing electrode assemblies is provided with a successively bent gap;
- an insulating and isolating layer covering the pressure-sensing layer and having a plurality of through holes, wherein some of the through holes are sequentially arranged along the gaps of the sensing electrode assemblies; and
- an elastic conductive layer covering the insulating and isolating layer;
- wherein when a portion of the elastic conductive layer is compressed by an external force, the compressed portion of the elastic conductive layer is brought into contact with the pressure-sensing layer through corresponding ones of the through holes such that the pressure-sensing layer generates said sensing signal and sends the sensing signal to the corresponding control module.

25. The monitoring system of claim 18, wherein each said sensor module comprises:
- a pressure-sensing layer provided in a corresponding said motion-sensing floor mat and having a corresponding said control module and a plurality of sensing electrode assemblies, wherein the corresponding control module is electrically connected to the sensing electrode assemblies, the sensing electrode assemblies are electrically connected to each of the information transmission modules of the corresponding motion-sensing floor mat such that the corresponding control module is electrically connected to each of the information transmission modules of the corresponding motion-sensing floor mat through the sensing electrode assemblies, and each of the sensing electrode assemblies is provided with a successively bent gap;
- an insulating and isolating layer covering the pressure-sensing layer and having a plurality of through holes, wherein some of the through holes are sequentially arranged along the gaps of the sensing electrode assemblies; and
- an elastic conductive layer covering the insulating and isolating layer;
- wherein when a portion of the elastic conductive layer is compressed by an external force, the compressed portion of the elastic conductive layer is brought into contact with the pressure-sensing layer through corresponding ones of the through holes such that the pressure-sensing layer generates said sensing signal and sends the sensing signal to the corresponding control module.

26. The monitoring system of claim 19, wherein each said sensor module comprises:
- a pressure-sensing layer provided in a corresponding said motion-sensing floor mat and having a corresponding said control module and a plurality of sensing electrode assemblies, wherein the corresponding control module is electrically connected to the sensing electrode assemblies, the sensing electrode assemblies are electrically connected to each of the information transmission modules of the corresponding motion-sensing floor mat such that the corresponding control module is electrically connected to each of the information transmission modules of the corresponding motion-sensing floor mat through the sensing electrode assemblies, and each of the sensing electrode assemblies is provided with a successively bent gap;
- an insulating and isolating layer covering the pressure-sensing layer and having a plurality of through holes, wherein some of the through holes are sequentially arranged along the gaps of the sensing electrode assemblies; and
- an elastic conductive layer covering the insulating and isolating layer;
- wherein when a portion of the elastic conductive layer is compressed by an external force, the compressed portion of the elastic conductive layer is brought into contact with the pressure-sensing layer through corresponding ones of the through holes such that the pressure-sensing layer generates said sensing signal and sends the sensing signal to the corresponding control module.

27. The monitoring system of claim 20, wherein each said sensor module comprises:
- a pressure-sensing layer provided in a corresponding said motion-sensing floor mat and having a corresponding said control module and a plurality of sensing electrode assemblies, wherein the corresponding control module is electrically connected to the sensing electrode assemblies, the sensing electrode assemblies are electrically connected to each of the information transmission modules of the corresponding motion-sensing floor mat such that the corresponding control module is electrically connected to each of the information transmission modules of the corresponding motion-sensing floor mat through the sensing electrode assemblies, and each of the sensing electrode assemblies is provided with a successively bent gap;
- an insulating and isolating layer covering the pressure-sensing layer and having a plurality of through holes, wherein some of the through holes are sequentially arranged along the gaps of the sensing electrode assemblies; and
- an elastic conductive layer covering the insulating and isolating layer;

wherein when a portion of the elastic conductive layer is compressed by an external force, the compressed portion of the elastic conductive layer is brought into contact with the pressure-sensing layer through corresponding ones of the through holes such that the pressure-sensing layer generates said sensing signal and sends the sensing signal to the corresponding control module.

28. The monitoring system of claim 21, wherein each said sensor module comprises:
- a pressure-sensing layer provided in a corresponding said motion-sensing floor mat and having a corresponding said control module and a plurality of sensing electrode assemblies, wherein the corresponding control module is electrically connected to the sensing electrode assemblies, the sensing electrode assemblies are electrically connected to each of the information transmission modules of the corresponding motion-sensing floor mat such that the corresponding control module is electrically connected to each of the information transmission modules of the corresponding motion-sensing floor mat through the sensing electrode assemblies, and each of the sensing electrode assemblies is provided with a successively bent gap;

an insulating and isolating layer covering the pressure-sensing layer and having a plurality of through holes, wherein some of the through holes are sequentially arranged along the gaps of the sensing electrode assemblies; and an elastic conductive layer covering the insulating and isolating layer;

wherein when a portion of the elastic conductive layer is compressed by an external force, the compressed portion of the elastic conductive layer is brought into contact with the pressure-sensing layer through corresponding ones of the through holes such that the pressure-sensing layer generates said sensing signal and sends the sensing signal to the corresponding control module.

* * * * *